US006777568B1

(12) United States Patent
Thoma et al.

(10) Patent No.: US 6,777,568 B1
(45) Date of Patent: Aug. 17, 2004

(54) TEMPLATED, LAYERED MANGANESE PHOSPHATE

(75) Inventors: Steven G. Thoma, Albuquerque, NM (US); Francois R. Bonhomme, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 289 days.

(21) Appl. No.: 10/174,685

(22) Filed: Jun. 18, 2002

(51) Int. Cl.[7] .................................................. C07F 9/06

(52) U.S. Cl. .................................... 556/24; 423/311

(58) Field of Search ......................... 423/311; 556/24

(56) References Cited

U.S. PATENT DOCUMENTS 4,089,881 A * 5/1978 Lukehart
4,497,743 A * 2/1985 Brisset et al.
5,780,003 A 7/1998 Lewis
6,156,931 A 12/2000 Lewis

OTHER PUBLICATIONS

Escobal, et al, "A New Manganese(II) Phosphate Templated by Ethylenediamine: $(C_2H_{10}\ N_2\ )[Mn_2(HPO_4)_3(H_2O]$. Hydrothermal Synthesis, Crystal Structure, and Spectroscopic and Magnetic Properties", Chem. Mater, (2000), 12, 376–382.

Serre, et al., "Synthesis and characterization of MIL–43 and MIL–44, two new layered templated tetravalent phosphates: $Zr(PO_4)\ _2\ N_2C_2H_{10}$ and $Ti_2(PO_4)\ _2\ (HPO_4)\ _2\ N_2C_2H_{10}$ ", Solid State Sciences 3 (2001), 623–632.

Simon, et al., "Synthesis and crystal structure of MIL–32: a new chiral layered aluminophosphate templated with non chiral tris (2–aminoethyl)amine: $Al_3\ (PO_4)\ _4,\ N_4C_6H_{21},\ H_2O$", Solid State Sciences 3 (2000), 389–395.

Yao–Hua Xu, et al., "An Open Framework Aluminophosphate with Unique 12–Membered Ring Channels: $Al_9(PO_4)_{12}\ (C_{24}H_{91}N_{16})$ 17 $H_2O$", Journal of Solid State Chemistry 145, (1999), 220–226.

Serpaggi, et al., "A New Gallium Phosphate Templated by Tris(2–aminoethyl)amine: $[Ga(HPO_4)(PO_4(OH)]$ $[(C_2H_7N)_3N]\ H_2O$", Acta Cryst.(1997), C52, 1568–1570.

S. Ayyappan, et al., "A Novel Monomeric Tin(II) Phosphate, $[N(C_2H_5NH_3)\ _3]\ ^{3+}\ [Sn(PO_4)(HPO_4)]\ ^{3-}\ 4H_4O$, Connected through Hydrogen Bonding," Journal of Solid State Chemistry 139, (1998), 207–210.

Simon, et al., "Synthesis and crystal structure of MIL–27: a new oxyfluorinated three–dimensional framework metallophosphate obtained with aluminum in four, five and sixfold coordination and templated with the tris (2–aminoethyl)amine", Solid State Sciences t. 1 (1999), 339–349.

* cited by examiner

Primary Examiner—Wayne A. Langel
(74) Attorney, Agent, or Firm—Elmer A. Klavetter

(57) ABSTRACT

A new crystalline maganese phosphate composition having an empirical formula:

$$Mn_3(PO_4)_4 \cdot 2(H_3NCH_2CH_2)_3N \cdot 6(H_2O).$$

The compound was determined to crystallize in the trigonal space group P-3c1 with a=8.8706(4) Å, c=26.1580(2) Å, and V (volume)=1783 Å$^3$. The structure consists of sheets of corner sharing Mn(II)O$_4$ and PO$_4$ tetrahedra with layers of (H$_3$NCH$_2$CH$_2$)$_3$N and water molecules in-between. The pronated (H$_3$NCH$_2$CH$_2$)$_3$N molecules provide charge balancing for the inorganic sheets. A network of hydrogen bonds between water molecules and the inorganic sheets holds the structure together.

12 Claims, 2 Drawing Sheets

TEMPLATED, LAYERED MANGANESE PHOSPHATE

This invention was made with Government support under Contract No. DE-AC04-94AL85000 awarded by the Department of Energy. The Government has certain rights in the invention.

BACKGROUND OF THE INVENTION

The invention describes a templated, layered manganese phosphate, and, more particularly, a layered manganese phosphate synthesized using tris(2-aminoethyl)amine as a template.

Manganese compounds are well known and are used in a variety of oxidative reactions. Manganese has stable oxidation states of +4, +3 and +2, allowing the effective use of manganese oxide. Manganese compounds can have layered structures or three-dimensional microporous structures. Manganese phosphate materials have been formed as crystalline structures, generally by hydrothermal synthesis (see Lewis, U.S. Pat. No. 5,780,003 and Lewis, U.S. Pat. No. 6,156,931). A variety of other metal phosphate compounds have been prepared, including aluminophosphates, gallophosphates, and tin phosphates.

These compounds are sometimes prepared using an organic molecule as a template to form an organo-metal phosphate compound. Escobal et al. (J. Escobal, J. Pizarro, J. Mesa, L. Lezama, R. Olazcuaga, M. Arriortua, and T. Rojo, Chem. Mater., 2000, 12, 376–382) describe a manganese phosphate compound templated by ethylenediamine. Serre et al. (C. Serre, F. Taulelle, and G. Ferey, Solid State Sciences, 2001, 3, 623–632) describe a zirconium phosphate compound, also templated by ethylenediamine. A variety of researchers have formulated other organo-metal phosphate compounds using tris(2-aminoethyl)amine (TREN) as the organic template. Simon et al. (N. Simon, T. Loiseau, and G. Ferey, Solid State Sciences, 2, 2000, 389–395) and Xu et al. (Y. Xu, B. Zhang, X. Chen, S. Liu, C. Duan, and X. You, J. of Solid State Chemistry, 1999, 145, 220–226) describe an alumino-phosphate compound using TREN as the template. Serpaggi et al. (F. Serpaggi, T. Loiseau, and G. Ferey, Acta Crystallographica Section C, 1997, C53, 1568–1570) describe a gallium-phosphate compound using TREN as the template. Ayyappan et al. (S. Ayyappan, A. Cheetham, S. Natarajan, and C. Rao, J. of Solid State Chemistry, 1998, 139, 207–210) describe a tin-phosphate compound using TREN as the template. These compounds have different structures and potentially different applications because of those structural differences.

DESCRIPTION OF SPECIFIC EMBODIMENTS

Figure 1:
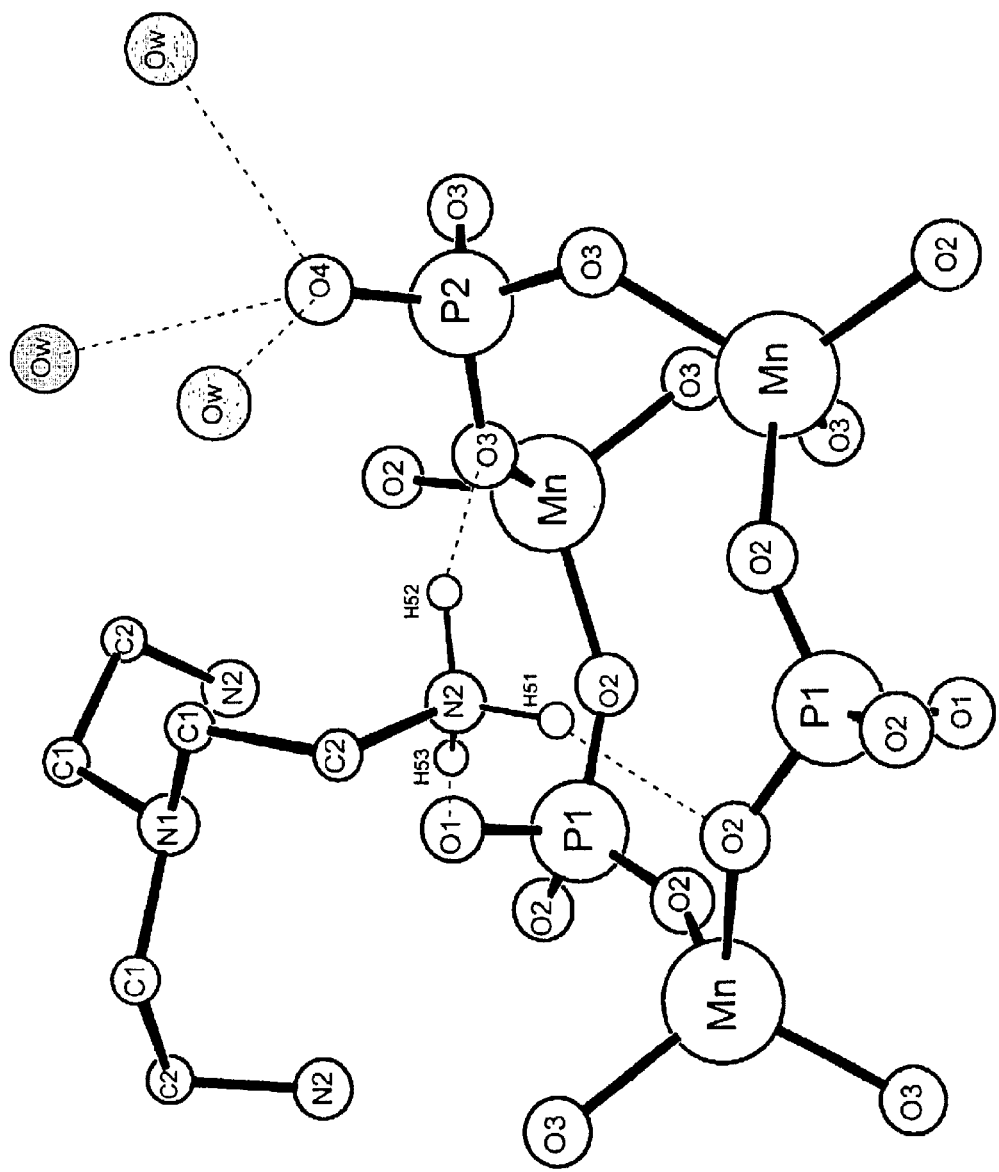
FIG. 1 shows a crystallographic representation of the structure of the composition of the present invention.

The present invention relates to a crystalline manganese phosphate composition and a process for preparing the composition. The composition has an empirical chemical composition on an anhydrous basis expressed by the formula $$Mn_3(PO_4)_4 \cdot 2(H_3NCH_2CH_2)_3N$$

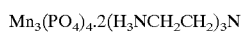

that is synthesized solvothermally or hydrothenmally using tris(2-aminoethyl)amine (TREN) as the organic template. The composition is a layered manganese phosphate compound. By a layered compound, it is meant that the compound is a crystalline material with atoms in the two-dimensional layers are cross-linked by chemical bonds, while the atoms of adjacent layers (in the third dimension) interact by physical forces only. A single layer is called a lamella or sheet. Each layer of the compound of the present invention comprises two-dimensional sheets of manganese phosphate that are sandwiched between a particular organic compound (i.e., TREN). These organo-manganese phosphate sheets are stacked on top of each other and separated from each other by a single layer of water molecules; that is, the layer of water molecules is interspersed between the $Mn_3(PO_4)_4 2(H_3NCH_2CH_2)_3N$ layers. When the compound is placed into liquid phase mixtures of certain molecules or mixture of molecules, preferential intercalation can occur, even at room temperature, with the composition of the present invention thereby acting as a separations material.

The as-synthesized manganese phosphate compound of the present invention is stable (that is, does not solubilize or otherwise break down) in aqueous solutons in the pH range of approximately 3.5 to approximately 9.5 and is entirely stable in non-aqueous solutions, including but not limited to pure and mixed alcohols, dioxanes, furans, glycols, ketones, xylenes, ethers, thiols, and amines. The compound is thermally stable at temperatures up to approximately 225° C. under air, oxygen, and inert atmospheres.

The composition of the present invention has an empirical chemical composition on a hydrated basis expressed by the formula $$Mn_3(PO_4)_4 \cdot 2(H_3NCH_2CH_2)_3N \cdot 6(H_2O).$$

The structure was solved ab initio from powder x-ray diffraction data and the compound characterized by scanning electron microscopy, elemental analysis and thermal analysis. The compound was determined to crystallize in the trigonal space group P-3c1 with a=8.8706(4) Å, c=26.1580(2) Å, and V (volume)=1783 Å$^3$. The structure consists of sheets of corner sharing Mn(II)O$_4$ and PO$_4$ tetrahedra with layers of TREN and water molecules in-between. The pronated TREN molecules provide charge balancing for the inorganic sheets. A network of hydrogen bonds between water molecules and the inorganic sheets holds the structure together.

The ab initio structure was determined from powder x-ray diffraction data with the positions of the first thirty-five peaks refined using a split Pearson VII function for the more asymmetric low angle peaks and a pseudo-Voigt function for the peaks above 15°. The peak positions were calibrated and the pattern indexed with good figures of merit. The refined lattice constants, as well as a summary of the crystallographic data, are given in Table 1. Table 2 shows atomic coordinates for non-hydrogen atoms for $Mn_3(PO_4)_4 \cdot 2(N_4C_6H_{21}) \cdot 6(H_2O)$.

TABLE 1

Crystal data and structure refinement parameters.

| Compound | $Mn_3(PO_4)_4 \cdot 2(N_4C_6H_{21}) \cdot 6(H_2O)$ |
|---|---|
| Chemical formula | $Mn_3P_4O_{22}N_8C_{12}H_{54}$ |
| Formula weight | 951.3 g/mole |
| Crystal system | Trigonal |
| Space group | P –3 c 1 (#165) |
| Unit cell dimensions | a = 8.8706(4) Å |
| | c = 26,158(2) Å |
| Volume | 1782.6 Å$^3$ |

TABLE 1-continued

Crystal data and structure refinement parameters.

| Z | 2 |
|---|---|
| Density (measured) | 1.80(1) g/cm$^3$ |
| Density (calculated) | 1.77 g/cm$^3$ |
| F(000) | 986 |
| Temperature | 298(2) K |
| Wavelength | CuK$_{\alpha1,\alpha2}$ |
| 2θ range | 2.5 to 80.0° |

TABLE 2

Atomic coordinates and isotropic displacement parameters for non-hydrogen atoms for Mn$_3$(PO$_4$)$_4$.2(N$_4$C$_6$H$_{21}$).6(H$_2$O).

| Atom-Site | x | y | z |
|---|---|---|---|
| Mn - 6f | 0.7415(5) | 0 | ¼ |
| P1 - 4d | ⅓ | ⅔ | 0.2373(4) |
| P2 - 4c | 0 | 0 | 0.1681(3) |
| O1 - 4d | ⅓ | ⅔ | 0.2957(6) |
| O2 - 12g | 0.304(1) | 0.491(1) | 0.2231(4) |
| O3 - 12g | 0.184(1) | 0.094(1) | 0.1899(3) |
| O4 - 4c | 0 | 0 | 0.1082(6) |
| Ow - 12g | 0.149(1) | 0.252(1) | 0.0359(3) |
| N1 - 4d | ⅔ | ⅓ | 0.0832(7) |
| N2 - 12g | 0.440(2) | 0.022(2) | 0.1517(3) |
| C1 - 12g | 0.515(2) | 0.163(1) | 0.0673(4) |
| C2 - 12g | 0.495(2) | 0.010(2) | 0.0990(3) |

Isotropic Atomic Displacement Parameters:
B(Mn)=2.8(1) Å$^2$; B(P)=2.9(1) Å$^2$; B(O)=3.1(2) Å$^2$; B(Ow)=3.1(3) Å$^2$; B(C)=B(N)=3.5(2) Å$^2$.

The elemental chemical analysis gave the atomic ration Mn/P=0.76. Thermo-gravimetric analysis showed a weight loss of 11.2 wt % below 200° C., attributed to water. With a measured density of 1.80(1) g/cm$^3$, the idealized composition was determined to be Mn$_3$(PO$_4$)$_4$ 2(H$_3$NCH$_2$CH$_2$)$_3$N.6(H$_2$). FIG. 1 shows an illustration of the crystallographic structure of the composition of the present invention. The ball-and-stick crystallographic illustration shows the relative positions of manganese (M), phosphorous (P), oxygen (O), carbon (C), nitrogen (N) and certain hydrogen (H) atoms. The numerical designations after the atomic designations indicate crystallographically equivalent atoms or atoms related by symmetry; for example, all O1 atoms are crystallographically equivalent. The designation Ow indicates oxygen from a water molecule. The hydrogen atoms shown are bonded to the terminal nitrogen atoms and show hydrogen bonding from the organic template to the inorganic part of the material.

Figure 2:
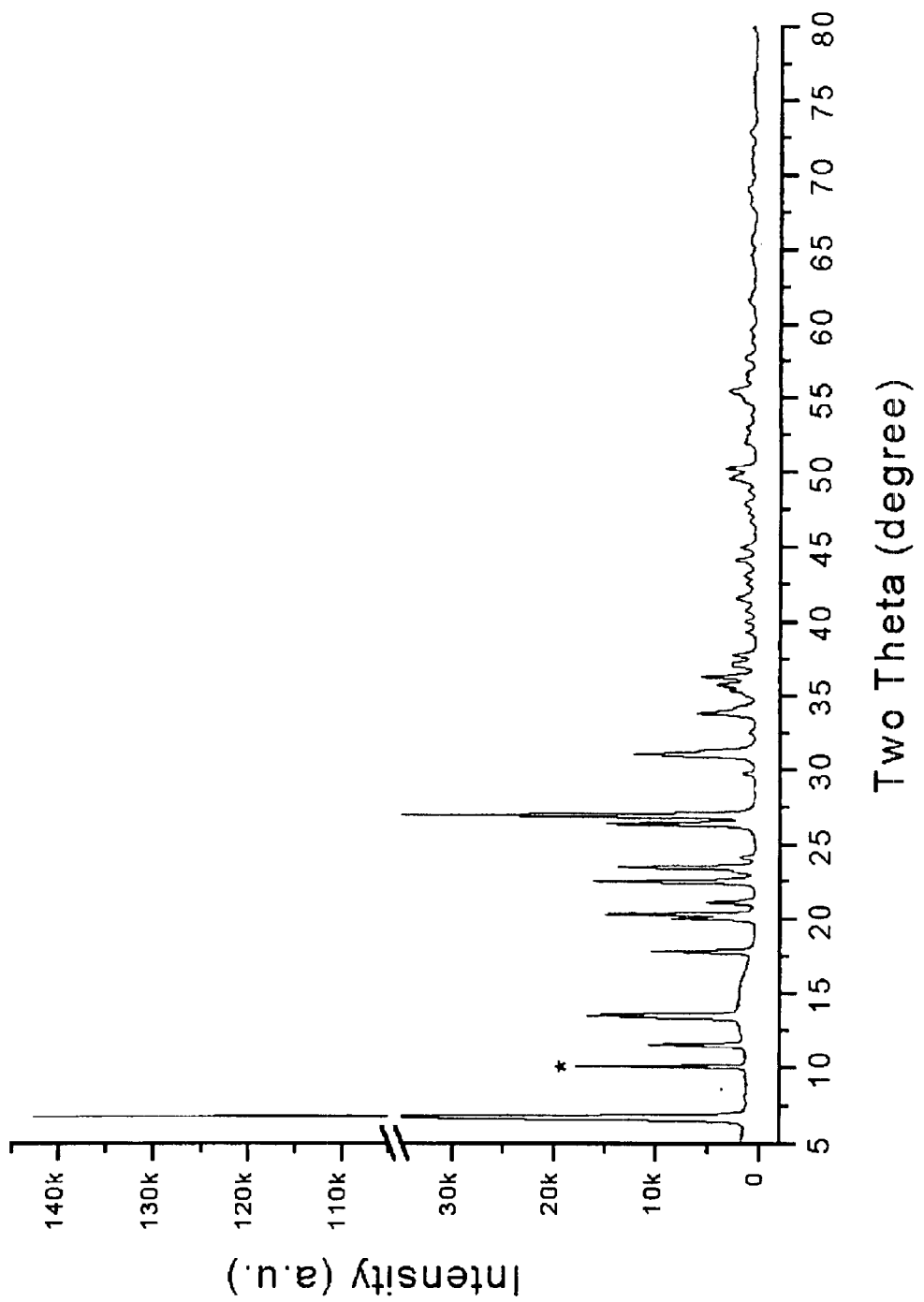
FIG. 2 shows an x-ray diffraction pattern of the composition of the present invention.

The x-ray diffraction pattern for this material is shown in FIG. 2. The observed positions in two theta degree of the main peaks are given by: 6.74, 11.51, 13.35, 13.53, 17.79, 20.03, 20.32, 21.13, 22.46, 23.44, 26.31, 26.89, and 30.96. The experimental error on the positions is approximately 0.02 degree. The sharp peak at 10.04 in the figure results from an impurity.

To prepare the composition of the present invention, a manganese compound, such as manganese carbonate was dissolved in a phosphorous-containing acid solution and a solvent added slowly, with addition of TREN. The formed solution was heated to a temperature greater than approximately 140° C. to form Mn$_3$(PO$_4$)$_4$.2(H$_3$NCH$_2$CH$_2$)$_3$N.6(H$_2$O). The compound was subsequently cooled, filtered, washed and dried. In one embodiment, 0.46 gm of manganese carbonate was dissolved in a solution of 3.0 gm of de-ionized water and 0.60 gm of phosphoric acid. 5.00 gm of pyridine was added slowly with stirring, followed by 0.58 gm of TREN. The molar ration of this formed precursor solution was 1.0 Mn:1.3P:1.0TREN:15.8 pyridine:42.9 water. The precursor solution was transferred to an autoclave, heated to approximately 170° C. for 5 days. After cooling to room temperature, the solid was recovered by vacuum filtration, washed with de-ionized water and acetone, and oven dried at 50° C.

The compound can be synthesized under a variety of conditions. For example, the pyridine to water ratio could be varied from approximately 0.4 to 44.2. H$_3$PO$_3$ could be substituted for H$_3$PO$_4$. Syntheses were performed with complete (molar) substitution of ethylene glycol for pyridine using ethylene glycol to water ratios of 3.0 to 24.2.

The thermal analysis results show three distinct weight loss events: an 11.2 wt % loss by 200° C.; a 27.8 wt % loss between 250 and 500° C.; and an additional 10.2 wt % loss between 550 and 700° C. The first event is attributed to the loss of interstitial water and agrees well with the calculated (11.4%) water content. The second event corresponds to the decomposition of TREN and agrees well with calculated (30.9 wt %) values. The final weight loss event is attributed to loss of oxygen due to framework condensation, consistent with condensation behavior observed in other organically templated metal phosphate systems. The measured elemental composition also agrees well with the calculated elemental composition derived from the structure determination (measured/calculated in wt %):
Mn(17.2/17.3), P(12.8/13.0), O(37.0/37.0), N(11.8/11.8), C(15.3/15.1), H(6.0/5.7).

The inorganic layer, of composition Mn$_3$(PO$_4$)$_4$, is built-up by alternating corner-sharing MnO$_4$ and PO$_4$ tetrahedra. The MnO$_4$ tetrahedron is fairly regular, with Mn—O distances of 2.02(1) Å and O—Mn—O angles ranging from 104.9(8)° to 116.7(7)°. The calculated bond valence sum for the Mn site is thus 2.16. In spinel type Mn$_3$O$_4$, the Mn$^{2+}$ site is also in a tetrahedral environment, with an average Mn—O distance of 2.04 Å. The MnO$_4$ group shares all its corners with phosphate groups, whereas each phosphate tetrahedron contains a terminal oxygen, with the P—O bond pointing along the c axis. This leads to an uncondensed inorganic layer containing 6-membered openings. The P2 atoms are located 2.14 Å above and below the mean plane of the layer (at z=¼ and ¾) whereas P1 is about 0.33 Å away from that plane.

The negatively charged manganese phosphate layer (Mn$_3$(PO$_4$)4)$^{6-}$ is sandwiched between two layers of triply protonated TREN molecules, with their ammonium groups pointing inwards. The central nitrogen atom of the TREN (N1) is located on a 3 fold axis, directly above the apical P1-O1 bond. The terminal ammonium groups point towards the center of the 6 membered rings of the inorganic layer (see FIG. 1). These neutral hybrid organic/inorganic layers are stacked along the c axis and separated from each other by a bilayer of water molecules.

The TREN molecules are strongly hydrogen bonded to the manganese phosphate layer. The minimum distance between the water molecules and the TREN ammonium groups is 3.98 Å, indicating that there is no hydrogen bonding between the organic template and the water molecules. The bridging O2 and O3 atoms, as well as the terminal O1 atom, hydrogen bond with the organic template whereas O4 does not (see FIG. 1). This terminal O4 is only surrounded by three water molecules that are within hydrogen bonding distance, with O4–Ow=2.71(1) Å. These three water molecules are separated by Ow–Ow=3.37 Å and therefore do not interact with each other. The cohesion of the water bilayer is ensured by hydrogen bonding, with Ow–Ow=2.70 Å. The organic is therefore bound to only one of the inorganic layers and does not contribute significantly to interlayer connectivity.

The interlayer stability is imparted solely via hydrogen bonding between the inorganic layer and the bilayer network of hydrogen bonded water molecules. This is contrary to the bonding scheme commonly observed among organically templated layered metal phosphates in which the organic cation bridges the inorganic layer by hydrogen bonding to adjacent layers. The difference in orientation of the organic is possibly due to the higher (density) charge compensation required by the $(Mn_3(PO_4)_4)^{6-}$ framework.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A crystalline manganese phosphate composition having an empirical composition on an anhydrous basis expressed by the empirical formula $Mn_3(PO_4)_4 \cdot 2(H_3NCH_2CH_2)_3N$.

2. A crystalline manganese phosphate composition having an empirical composition on a hydrated basis expressed by the empirical formula $Mn_3(PO_4)_4 \cdot 2(H_3NCH_2CH_2)_3N \cdot 6(H_2O)$.

3. The crystalline manganese phosphate composition of claim 1 comprising two-dimension sheets of $Mn_3(PO_4)_4^{6-}$ anion interspersed between $(H_3NCH_2CH_2)_3N^{3+}$ ions to form organo-manganese phosphate sheets.

4. The crystalline manganese phosphate composition of claim 3 wherein a single layer of water molecules are interspersed between said organo-manganese phosphate sheets.

5. The crystalline manganese phosphate composition of claim 1 characterized in that the composition is stable in an aqueous solution in the pH range of approximately 3.5 to approximately 9.5.

6. The crystalline manganese phosphate composition of claim 1 characterized in that the composition is stable in a nonaqueous solution.

7. The crystalline manganese phosphate composition of claim 6 wherein said nonaqueous solution is selected from the group consisting of alcohols, dioxanes, furans, glycolfs, ketones, xylenes, ethers, thiols, amines, and mixtures thereof.

8. The crystalline manganese phosphate composition of claim 1 characterized in that the composition is thermally stable at temperatures up to approximately 225° C.

9. The crystalline manganese phosphate composition of claim 1 characterized in that the composition is crystallized in the trigonal space group P-3c1 with a=8.8706(4) Å and c=26.1580(2) Å.

10. A crystalline manganese phosphate composition produced by the process comprising:

dissolving a manganese-containing compound and $(H_3NCH_2CH_2)_3N$ in a phosphorous-containing solution; and heating to a temperature greater than approximately 140° C.

11. The crystalline manganese phosphate composition of claim 10 wherein said manganese-containing compound is manganese carbonate.

12. The crystalline manganese phosphate composition of claim 10 wherein said phosphorous-containing solution comprises an acid selected from the group consisting of phosphoric and phosphorous acid and a solvent selected from the group consisting of pyridine, ethylene glycol, and water.

* * * * *